United States Patent [19]
Cox et al.

[11] Patent Number: 5,688,962
[45] Date of Patent: Nov. 18, 1997

[54] CYCLIZATION PROCESS FOR MAKING OXAZOLIKINONES

[75] Inventors: John Michael Cox, Bracknell; David Philip John Pearson, Holyport; Anthony Marian Kozakiewicz, Wokingham; Richard Butler Moore, Congleton; Glynn Mitchell, Cookham; David William Langton, Reading; Russell Ellis, Bracknell, all of United Kingdom

[73] Assignee: Zeneca Limited, London, England

[21] Appl. No.: 649,843

[22] Filed: May 16, 1996

[30] Foreign Application Priority Data

May 26, 1995 [GB] United Kingdom ............... 9510750

[51] Int. Cl.$^6$ .................. C07D 263/04; C07D 263/16; C07D 263/46
[52] U.S. Cl. .................. 548/225; 548/226; 548/228; 548/233
[58] Field of Search .................. 548/225, 226, 548/228, 233

[56] References Cited

FOREIGN PATENT DOCUMENTS 94 13652  6/1994  WIPO .
95 33719  12/1995  WIPO .

*Primary Examiner*—Johann Richter
*Assistant Examiner*—Jane C. Oswecki
*Attorney, Agent, or Firm*—Joseph R. Snyder

[57] ABSTRACT

A process for the synthesis of a compound of general formula II:

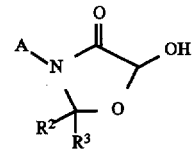

wherein:

$R^2$ and $R^3$ are each independently hydrogen or $C_1$–$C_4$ alkyl;

A is an aromatic or heteroaromatic ring system optionally substituted with one or more substituents as defined herein; and in which any ring nitrogen atom may be quaternised or oxidised;

alternatively, any two substituents of the group A may combine to form a fused 5- or 6-membered saturated or partially saturated carbocyclic or heterocyclic ring in which any carbon or quaternised nitrogen atom may be substituted with any of the groups defined herein for A or in which a ring carbon atom may be oxidised;

the process comprising cyclising a compound of general formula VII:

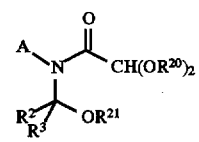

wherein A, $R^2$ and $R^3$ are as defined for general formula II, $R^{20}$ is hydrogen, benzyl or benzyl substituted with up to five substituents selected from halo, $C_1$–$C_6$ alkyl, O($C_1$–$C_6$ alkyl) or nitro and $R_{21}$ is $C_1$–$C_8$ alkyl, benzyl or benzyl substituted with up to five of the substituents mentioned above for $R^{20}$.

11 Claims, No Drawings

CYCLIZATION PROCESS FOR MAKING OXAZOLIKINONES

The present invention relates to an process for the preparation of oxazolidinone compounds. In particular, the invention relates to the preparation of compounds which are useful as intermediates in the synthesis of agrochemicals such as herbicides.

WO-A-9413652 and UK patent application No 9501158 both relate to herbicides and include within their scope compounds of general formula I:

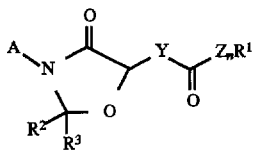

wherein
Z is O, S or $NR^4$;
$R^4$ is hydrogen or $C_1-C_4$ alkyl;
n is 0 or 1;
Y is O, S or $NR^6$;
$R^6$ is H, CHO, or $C_1-C_{10}$ hydrocarbyl, which may be substituted with up to two substituents chosen from $OR^{16}$, $COR^{16}$, $COOR^{16}$, $OCOR^{16}$, CN, halogen, $S(O)_pR^{16}$, $NR^{16}R^{17}$, $NO_2$, $NR^{16}COR^{17}$, $NR^{16}CONR^{17}R^{18}$, $CONR^{16}R^{17}$ or heterocyclyl;
$R^{16}$, $R^{17}$ and $R^{18}$ are each, independently, hydrogen, $C_1-C_6$ hydrocarbyl or $C_1-C_6$ halohydrocarbyl;
p is 0, 1 or 2;
alternatively:
when Y is $NR^6$ and either Z is $NR^4$ or n is 0, $R^6$ and the substituents of Z or $R^1$ may together form a bridge represented by the formula $-Q^1-Q^2-$ or $-Q^1-Q^2-Q^3-$, where $Q^1$, $Q^2$, and $Q^3$ each independently represent $CR^{12}R^{13}$, $=CR^{12}$, CO, $NR^{14}$, $=N$, O or S;
each of $R^{12}$ and $R^{13}$ independently represents hydrogen, $C_1-C_4$ alkyl, OH or halogen;
$R^4$ represents hydrogen or $C_1-C_4$ alkyl;
$R^1$ is hydrogen or $C_1-C_{10}$ hydrocarbyl or heterocyclyl having 3 to 8 ring atoms, either of which may optionally be substituted with halogen (i.e. chlorine, bromine, fluorine or iodine), hydroxy, $SO_2NR^aR^b$ (where $R^a$ and $R^b$ are independently H or $C_1-C_6$ alkyl), $SiR^c_3$ (where each $R^c$ is independently $C_1-C_4$ alkyl or phenyl), cyano, nitro, amino, mono- and dialkylamino in which the alkyl groups have from 1 to 6 or more carbon atoms, acylamino, $C_1-C_6$ alkoxy, $C_1-C_6$ haloalkoxy, $C_1-C_6$ alkylthio, $C_1-C_6$ alkylsulphinyl, $C_1-C_6$ alkylsulphonyl, carboxy, carboxyamide, in which the groups attached to the N atom may be hydrogen or optionally substituted lower hydrocarbyl; alkoxy carbonyl wherein the alkoxy group may have from 1 to 6 or more carbon atoms, or aryl such as phenyl; $R^2$ and $R^3$ are each independently hydrogen or $C_1-C_4$ alkyl;
A is an aromatic or heteroaromatic ring system optionally substituted with one or more substituents selected from: halogen or $C_1-C_{10}$ hydrocarbyl, $-O(C_1-C_{10}$ hydrocarbyl), $-S(C_1-C_{10}$ hydrocarbyl), $-SO(C_1-C_{10})$ or $-SO_2(C_1-C_{10}$ hydrocarbyl), cyano, nitro, SCN $SiR^c_3$ (where each $R^c$ is independently $C_1-C_4$ alkyl or phenyl), $COR^7$, $CR^7NOR^8$, NHOH, $ONR^7R^8$, $SF_5$, $COOR^7$, $SO_2NR^7R^8$, $SO_2NR^7R^8$, $OR^9$ or $NR^{10}R^{11}$; and in which any ring nitrogen atom may be quaternised or oxidised;
alternatively, any two substituents of the group A may combine to form a fused 5- or 6-membered saturated or partially saturated carbocyclic or heterocyclic ring in which any carbon or quaternised nitrogen atom may be substituted with any of the groups mentioned above for A or in which a ring carbon atom may be oxidised;
$R^7$ and $R^8$ are each independently hydrogen or $C_1-C_{10}$ hydrocarbyl;
$R^9$ is hydrogen, $C_1-C_{10}$ hydrocarbyl, $SO_2(C_1-C_{10}$ hydrocarbyl), CHO, $CO(C_1-C_{10}$ hydrocarbyl), COO $(C_1-C_{10}$ hydrocarbyl) or $CONR^7R^8$;
$R^{10}$ and $R^{11}$ are each independently hydrogen, $C_1-C_{10}$ hydrocarbyl, $O(C_1-C_{10}$ hydrocarbyl), $SO_2(C_1-C_{10}$ hydrocarbyl), CHO, $CO(C_1-C_{10}$ hydrocarbyl), COO $(C_1-C_{10}$ hydrocarbyl) or $CONR^7R^8$;
any of the hydrocarbyl groups within the group A may optionally be substituted with halogen (i.e. chlorine, bromine, fluorine or iodine), hydroxy, $SO_2NR^aR^b$ (where $R^a$ and $R^b$ are independently H or $C_1-C_6$ alkyl), cyano, nitro, amino, mono- and dialkylamino in which the alkyl groups have from 1 to 6 or more carbon atoms, acylamino, $C_1-C_6$ alkoxy, $C_1-C_6$ haloalkoxy, $C_1-C_6$ alkylthio, $C_1-C_6$ alkylsulphinyl, $C_1-C_6$ alkylsulphonyl, carboxy, carboxyamide, in which the groups attached to the N atom may be hydrogen or lower hydrocarbyl optionally substituted with halogen; alkoxy carbonyl wherein the alkoxy group may have from 1 to 6 or more carbon atoms, or aryl such as phenyl.

The expression "$C_1-C_{10}$ hydrocarbyl" in the foregoing definitions, whether the expression is used on its own or as part of a larger radical such as, for example, $C_1-C_{10}$ hydrocarbyloxy, is intended to include hydrocarbyl radicals of up to ten carbon atoms. Subclasses of such hydrocarbyl radicals include radicals with up to four or up to six carbon atoms. The expression "hydrocarbyl" is intended to include within its scope aliphatic, alicyclic, and aromatic hydrocarbyl groups and combinations thereof. It thus includes, for example, alkyl, alkenyl, and alkynyl radicals, cyclopropyl, cyclopropylmethyl, cyclobutyl, cyclopentyl, and cyclohexyl radicals, the adamantyl radical and the phenyl radical. The expression "heterocyclyl" in the foregoing definitions is intended to include both aromatic and non-aromatic radicals. Examples of heteroaromatic radicals include pyridyl, pyrimidyl, triazinyl, thienyl, furyl, oxazolyl, isoxazolyl, and thiazolyl and examples of non-aromatic radicals include partially and fully saturated variants of the above.

The expression "$C_1-C_6$ alkyl" refers to fully saturated straight or branched hydrocarbon chains having from one to six carbon atoms. Examples include methyl, ethyl, n-propyl, iso-propyl, t-butyl and n-hexyl. Expressions such as "alkoxy", "cycloalkyl" "alkylthio" "alkylsulphonyl", "alkylsulphinyl" and "haloalkyl" should be construed accordingly.

The expression "$C_2-C_6$ alkenyl" refers to a straight or branched hydrocarbon chain having from two to six carbon atoms and at least one carbon-carbon double bond. Examples include ethenyl, 2-propenyl and 2-hexenyl. Expressions such as cycloalkenyl, alkenyloxy and haloalkenyl should be construed accordingly.

The expression "$C_2-C_6$ alkynyl" refers to a straight or branched hydrocarbon chain having from two to six carbon atoms and at least one carbon-carbon triple bond. Examples include ethynyl, 2-propynyl and 2-hexynyl. Expressions such as haloalkynyl, alkynyloxy and haloalkynyl should be construed accordingly.

Subclasses of the above include alkyl, alkenyl or alkynyl groups with up to 4 or up to 2 carbon atoms.

In the context of the present specification the terms "aryl" and "aromatic ting system" refer to ring systems which may be mono-, bi- or tricyclic. Examples of such ring systems include phenyl, naphthalenyl, anthracenyl or phenanthrenyl. Nitrogen atoms in the ring may be quaternised or oxidised.

In the context of the present specification, the term "heteroaryl" refers to an aromatic ring system containing at least one heteroatom and consisting either of a single ring or of two 5 or more fused rings. Preferably, single rings will contain up to four and bicyclic systems up to five heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, 1,2,3,4-oxatriazolyl, 1,2,3,5-oxatriazolyl, 1,2,3,4-thiatriazolyl, 1,2,3,5-thiatriazolyl, pyridyl, pyrimidinyl, pyridazinyl, pyrazinyl, 1,2,3-triazinyl, 1,2,4-triazinyl, 1,3,5-triazinyl, 1,2,4,5-tetrazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the context of the present specification, the term "fused saturated or partially saturated carbocyclic or heterocyclic ring" refers to a fused ring system in which a 5- or 6-membered carbocyclic or heterocyclic ring system is fused to a benzene ring. Examples of such systems include benzimidazolinyl, benzoxazolinyl and benzodioxolyl.

WO-A-9413652 teaches various synthetic methods for the preparation of such compounds. For example, compounds of general formula I may be prepared from compounds of general formula II:

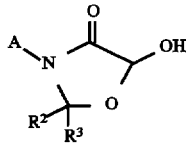
II wherein A, $R^2$ and $R^3$ are as defined in general formula I.

The prior art document suggests that compounds of general formula II may be prepared by the reaction of a compound of general formula III:

 III wherein A is as defined above for general formula I; with a compound of general formula IV:

 IV wherein $R^2$ and $R^3$ are as defined above for general formula I; and glycolic acid to give a compound of general formula V:

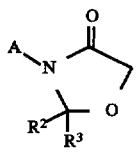
V wherein A, $R^2$ and $R^3$ are as defined in general formula I. The compound of general formula V may then be convened into a compound of general formula II by reaction firstly with a strong base and then with a compound of the formula VI:

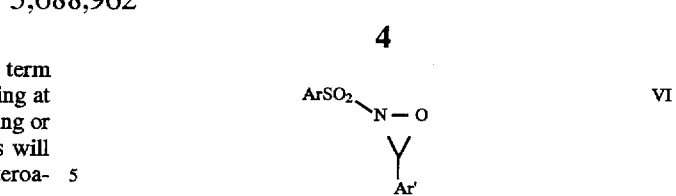

wherein Ar is, for example a p-tolyl group and Ar' is a phenyl group.

However, this method for the preparation of compounds of general formula I is not always convenient because, although the conversion of the compounds of general formula II to compounds of general formula I is relatively efficient and high yielding, the reaction between the compounds of general formulae III and IV and glycolic acid is often low yielding and would be difficult to adapt for use on an industrial scale. The reaction between the compounds of general formulae V and VI is also not particularly well suited to large scale use.

Therefore, for the efficient large scale manufacture of compounds of general formula I, an improved process for the production of intermediates of general formula II is needed.

Therefore, in a fast aspect of the present invention, there is provided a process for the synthesis of a compound of general formula II as defined above, the process comprising cyclising a compound of general formula VII:

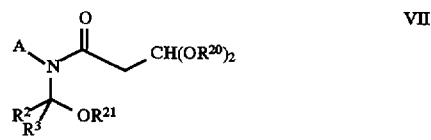
VII wherein A, $R^2$ and $R^3$ are as defined for general formula I, $R^{20}$ is hydrogen, benzyl or benzyl substituted with up to five substituents selected from halo, $C_1$–$C_6$ alkyl, $O(C_1$–$C_6$ alkyl) or nitro and $R^{21}$ is $C_1$–$C_8$ alkyl, benzyl or benzyl substituted with up to five of the substituents mentioned above for $R^{20}$.

When $R^{20}$ is benzyl or substituted benzyl, the cyclisation may be achieved by reduction and a particularly suitable reduction method is hydrogenation. The hydrogenation may be carried out over a catalyst, suitably a palladium catalyst, in the presence of an acid, for example trifluoroacetic acid. Solvents include those whose use is standard in hydrogenation reactions, for example lower alkanols (e.g. methanol or ethanol) or chlorinated lower hydrocarbons (eg dichloromethane). Some experimentation may be necessary to determine the best solvent for any particular reaction, but this will be a matter of routine for those skilled in the art. When $R^{20}$ is benzyl or substituted benzyl, it is preferred that $R^{21}$ is also benzyl or substituted benzyl and, most preferred that it is identical to $R^{20}$.

Certain substituted benzyl groups may be removed under other conditions; methoxybenzyl by treatment with acid, for example trifluoroacetic acid, or by oxidative methods, for example using concentrated ammonium nitrate or dichloro- or dicyano-quinone; o-nitrobenzyl may be removed by photolysis.

On the other hand, when $R^{20}$ is hydrogen, the cyclisation may be carded out by reaction with an acid, for example hydrochloric acid, particularly gaseous hydrogen chloride, in an organic solvent such as 1,4-dioxan. When $R^{20}$ is hydrogen, it is preferred that $R^{21}$ is $C_1$–$C_8$ alkyl.

The cyclisation of a compound of general formula VII, provides the compound of general formula II in high yield and is also relatively cheap and simple to conduct.

Compounds of general formula VII may be prepared from compounds of general formula VIII:

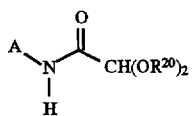

wherein A and $R^{20}$ are as defined above, by reaction with compounds of formula IX:

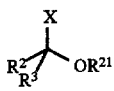

where X is a leaving group such as a halogen, particularly chlorine, and $R^2$, $R^3$ and $R^{21}$ are as defined above. For optimal results, the reaction may be carried out in a mixed aqueous/organic solvent, for example water/dichloromethane and in the presence of a base such as sodium hydroxide and a phase transfer catalyst such as tetrabutylammonium iodide. Compounds of general formula IX are readily available or may be prepared by known methods by the skilled chemist.

Compounds of general formula VIII may be prepared from compounds of general formula III by reaction with compounds of general formula X:

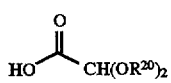

wherein $R^{20}$ is as defined above for general formula VII. The compound of general formula X may be converted to the acid chloride using a chlorinating agent such as oxalyl chloride in the presence of N,N-dimethylformamide (DMF) before reaction with the compound of general formula III. The reaction may take place in an organic solvent, preferably a chlorinated solvent such as dichloromethane. Alternatively, compounds of general formula VIII may be prepared by bringing a compound of formula III together in solution with a compound of formula X in the presence of dicyclohexylcarbodiimide (DCC). The DCC is coverted to dicyclohexylurea which may be readily separated from the reaction mixture, and the product (VIII) recovered from the reaction solution. Suitable solvents for this process include chlorianted hydrocarbons (eg. dichloromethane) and ethers (eg. diethyl ether).

Carboxylic acids of general formula X may be prepared from esters of general formula XI:

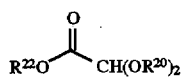

wherein $R^{20}$ is defined above and $R^{22}$ is hydrogen, benzyl or benzyl substituted with up to five substituents selected from halo, $C_1-C_6$ alkyl, $O(C_1-C_6$ alkyl) or nitro; by known methods such as treatment with aqueous potassium carbonate in a solvent such as tetrahydrofuran (THE).

Esters of general formula XI may be prepared from dichloroacetic acid by reaction with a mixture of an alcohol of general formula $R^2OH$, where $R^{20}$ is as deemed above for general formula VII, and its corresponding alkali metal alkoxide. The reaction will usually be conducted in the appropriate alcohol. All of the starting materials of this reaction are readily available.

The route described above is particularly suitable for the preparation of compounds of general formula VII in which $R^{20}$ is benzyl or substituted benzyl. It may be preferable to synthesise compounds in which $R^{20}$ is hydrogen from compounds of general formula XII:

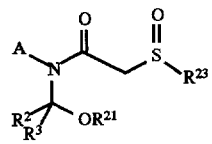

wherein A, $R^2$ and $R^3$ are as deemed for general formula I, $R^{21}$ is as deemed above and $R^{23}$ is $C_1-C_6$ alkyl, benzyl, or aryl such as phenyl, any of which may optionally be substituted by the substituents mentioned above for $R^{20}$; by a two stage process in which the compound is either treated with a strong acid or with an acylating agent and then heated with a weak base. The reagent used may be hydrochloric acid, typically of about 2M concentration, or, preferably, trifluoroacetic anhydride in an organic solvent such as tetrahydrofuran (THF). The reaction may be carried out at a temperature of from about 5° to 40° C., more usually from about 15° to 25° C. In the second stage, the reaction mixture is neutralised with a base, typically a weak aqueous base such as sodium bicarbonate. The base may be added to the reaction mixture at a temperature of from about 15° to 25° C. before heating the mixture to the reflux temperature of the solvent.

In some cases, treatment of a compound of general formula XII with a strong acid will result in the production of a compound of general formula II without isolation of the intermediate of general formula VH. However, particularly in cases where the group A has electron withdrawing substituents such as trifluoromethyl, this can lead to problems with side reactions, for example acid hydrolysis, and therefore to low yields of the required product of general formula II. It is greatly preferred, therefore, that milder conditions, such as the use of gaseous hydrogen chloride in an anhydrous solvent, are employed since this ensures that the yield is significantly higher.

Compounds of general formula XII may be obtained by the oxidation of compounds of general formula XIII:

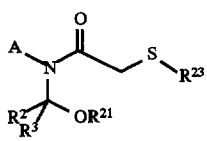

wherein A, $R^{21}$ and $R^{23}$ are as defined above using, for example, an oxidising agent such as sodium periodate. The reaction may be carried out in a polar solvent such as a mixture of water and an alcohol, for example methanol or ethanol, at a temperature of from 0° to 100° C. Often, the periodate will be added to the compound of general formula XIII with cooling to between 0° and 10° C. before allowing the reaction mixture to warm to about 15° to 25° C.

Compounds of general formula XIII may be prepared from compounds of general formula XIV:

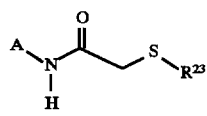

wherein A and $R^{23}$ are as defined above; by reaction with a compound of general formula IX as defined above. The reaction requires basic conditions which may be provided by, for example, aqueous sodium hydroxide which may be mixed with an organic solvent such as dichloromethane. In this case, a phase transfer catalyst, for example benzyltriethylammonium chloride, may also be present. The reaction may be carried out at a temperature of from about 10° to 30° C., preferably at about 20° C.

Compounds of general formula XIV may be synthesised by reacting a compound of general formula III with a compound of general formula XV:

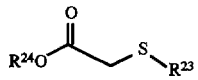   XV wherein $R^{23}$ is as defined above and $R^{24}$ is $C_1$–$C_6$ alkyl. The reaction may be conducted in an organic solvent such as dimethylsulphoxide (DMSO) and in the presence of a base, for example sodium hydride. The preferred reaction temperature is from 10° to 30° C., generally about 20° C. Compounds of general formulae III and XV are readily available or may be prepared using literature methods by the skilled chemist.

Once obtained by the method of the present invention, compounds of general formula II may be convened to herbicides of general formula I in a variety of ways.

Therefore, in a second aspect of the invention, there is provided a process for the preparation of a compound of general formula I as defined above, the process comprising synthesising a compound of general formula II by the process of the first aspect of the invention and subsequently convening the compound of general formula II to a compound of general formula I by any suitable method.

In one method, a compound of general formula II may be reacted with a compound of the general formula XVI, XVII, XVIII or XIX:

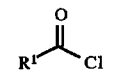   XVI

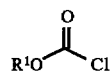   XVII $R^1$—N=C=O   XVIII

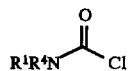   XIX wherein $R^1$ is as defined above for general formula I; resulting in the production of compounds of general formula I in which Y is O and in which n is O, Z is O, Z is NH and Z is $NR^4$ respectively.

Similarly, a compound of general formula II may be reacted with a compound of general formula XX:

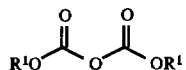   XX wherein $R^1$ is as defined above for general formula I. This gives a compound of general formula I in which Y and Z are both O.

These reactions may be conducted in an organic solvent such as dichloromethane. When reacting the compound with an isocyanate of general formula XVIII, it may be advantageous to include in the reaction mixture a catalytic amount of boron trifluoride etherate.

Compounds of general formula II may be converted into compounds of general formula XXI:

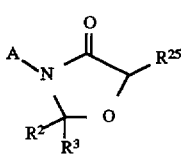   XXI wherein $R^2$ and $R^3$ are as defined for general formula I and $R^{25}$ is chloro, methane sulfonyloxy or toluene sulfonyloxy. The compounds in which $R^{25}$ is methane or toluene sulfonyloxy may be obtained by reaction with methane sulfonyl chloride or toluene sulfonyl chloride as appropriate although, in some cases, the compound in which $R^{25}$ is chloro may be obtained, particularly in the reaction with methane sulfonyl chloride. The reaction may be conducted at a temperature of from 0° to 30° C., usually at about 5° C., in an organic solvent such as dichloromethane and in the presence of a base such as triethylamine.

Compounds of general formula XXI may be converted into compounds of general formula XXII:

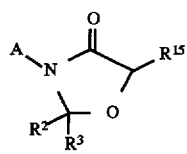   XXII wherein $R^2$ and $R^3$ are as deemed for general formula I and $R^{15}$ is $NHR^6$ where $R^6$ is as defined in general formula I; by reaction with ammonia or an amine of formula $NH_2R^6$. The reaction may be carried out at a temperature of from 0° to 80° C., preferably from 0° C. to 50° C. It is often the case that the reaction is initiated at 0° C. and subsequently allowed to warm to room temperature after most of the reactant has been converted to product. Usually, the reaction will take place in an organic solvent, particularly an ether such as diethyl ether or tetrahydrofuran (THF).

Compounds of general formula XXII may be converted to compounds of general formula I in which Y is $NR^6$ by reaction with a compound of general formula XVI, XVII, XVIII or XIX using the reaction conditions described above for the conversion of a compound of general formula II to a compound of general formula I.

Compounds of general formula I may also be converted to other compounds of general formula I. For example, bridged compounds of general formula I in which Y is $NR^6$ and Z is $NR^4$ and $R^4$ and $R^6$ form a bridge may be synthesised in a variety of ways.

Compounds in which the bridge is represented by the formula —$Q^1$—C(=O)— may be synthesised from compounds of general formula I in which Z is NH and Y is N—$Q^1$—C(=O)—L in which L is a leaving group such as methoxy, ethoxy, chloro and $Q^1$ is as defined above. The reaction is preferably carried out in the presence of a strong base such as sodium hydride, suitably in a solvent such as THF. Usually, the reaction temperature will be in the range of 0° to 80° C., preferably room temperature. They may alternatively be synthesised from compounds of general formula (II) in which $R^{21}$ is a leaving group such as I or Br by reaction with an imidazolinedione of general formula XXIII:

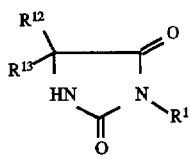

XXIII where each of $R^{12}$ and $R^{13}$ independently represent hydrogen or $C_1$-$C_4$ alkyl. The reaction is carried out in an organic solvent such as N,N-dimethylformamide or tetrahydrofuran, in the presence of a strong base such as sodium hydride.

Compounds in which the bridge is represented by the formula —C(=O)—C(=O)— or —C(=O)—$Q^2$—C(=O)— may be synthesised from compounds of general formula I in which both Y and Z are NH by reaction with a compound of formula LC(=O)—C(=O)L or LC(=O)—$Q^2$—C(=O)L in which $Q^2$ and L are as defined above. The reaction may be carried out in an organic solvent such as toluene at a temperature of from 30° to 120° C. Often, the reaction will be conducted at a temperature of about 80° C.

Compounds in which the bridge is represented by the formula —HC=CH— may be synthesised from compounds of general formula I in which Z is NH and Y is $NCH_2CHL_2$, wherein L is a leaving group as defined above. The reaction may be carried out in a solvent such as THF under acidic conditions which may be provided by the presence of an aqueous inorganic acid such as hydrochloric acid. The reaction temperature may be from 5° to 50° C. but will, in most cases, be room temperature.

Compounds of general formula I in which the bridge is represented by the formula —CH=CH— may be converted to compounds of general formula I in which the bridge is represented by $CH_2$—$CH_2$ by reduction, for example hydrogenation over a palladium or platinum catalyst. Catalytic hydrogenations may be carried out in a solvent such as ethyl acetate. The reaction usually proceeds at an acceptable rate at room temperature and at a pressure of from 1 to 5 bar.

Compounds in which the bridge is represented by the formula —C(=O)$CH_2$— may be synthesised from compounds of general formula I in which Y and Z are both NH by reaction with CHO—CHO. The reaction may be conducted under acidic conditions which may be provided by the presence of a catalytic amount of, for example, 1-toluene sulphonic acid. An example of a suitable reaction solvent is toluene and the reaction is preferably carried out under Dean and Stark conditions at a temperature of from about 80° to 120° C., typically at 110° C. Similar reaction conditions may also be used for the synthesis of compounds of general formula I in which the bridge is represented by the formula —$CH_2$—$OCH_2$—. However, in this case, paraformaldehyde is used in place of the CHO—CHO. This particular reaction may be adapted by those skilled in the art for the synthesis of other bridged compounds.

The invention will now be described in more detail in the following examples.

EXAMPLE 1

Preparation of 5-t-Butylcarbamoyloxy-3(3-trifluoromethylphenyl)oxazolidin-4-one

Step 1 Preparation of benzyl dibenzyloxyacetate

A solution of dichloroacetic acid (12.89 g) in benzyl alcohol (50 ml) was added to a solution of sodium benzyloxide from sodium hydride (13.53 g, 55% dispersion in mineral oil) in benzyl alcohol (150 ml). The resultant mixture was heated at 190° C. for four hours, then the solvent distilled off under reduced pressure. The residue was triturated with ether the solid removed by filtration and distributed between hydrochloric acid (2 N) and ether. The extracts were dried over magnesium sulphate and evaporated under reduced pressure. The residue was chromatographed on silica, using dichloromethane as eluant, to give benzyl dibenzyloxyacetate (12.50 g) as a colourless oil. None of the expected corresponding acid was eluted with more polar solvents.

NMR ($CDCl_3$): δ 4.7(4 H, dd), 5.1(1 H,s),5.2(2 H,s), 7.3(15 H,m). MS: $M^+$362

NB When the residue was triturated with ether, it appears that some of the ester product may have been lost; the work-up procedure should be modified in view of ester, rather than acid, being produced.

Step 2 Preparation of dibenzyloxyacetic acid

Water (20 ml) and potassium carbonate (10.64 g) were added to a solution of benzyl dibenzyloxyacetate (11.15 g, prepared as described in Step 1 above) in tetrahydrofuran (80 ml) and the mixture heated under reflux for twenty-four hours. It was allowed to cool, poured into water, extracted with ether, acidified with concentrated hydrochloric acid and again extracted with ether. The extract from acidic solution was washed with brine, dried over magnesium sulphate and evaporated under reduced pressure to give the title compound (8.12 g), used crude in Step 3.

NMR ($CDCl_3$): δ 4.7(4 H,m), 5.1 (1 H,bs), 7.3(10 H,m), 9.2(1 H,bs).

Step 3 Preparation of 2,2-dibenzyloxy-N(3-trifluoromethylphenyl)acetamide

A stirred solution of dibenzyloxyacetic acid (4.0 g, prepared as described in Step 2) in dichloromethane (40 ml) was cooled to 0° C. and treated dropwise with, successively, 4-N,N-dimethylformamide (100 mg) and oxalyl chloride (2.0 g). After thirty minutes, pyridine (3.52 g), 3-trifluoromethyl aniline (2.64 g) and 4-dimethylaminopyridine (100 mg) were added. The mixture was stirred at 0° C. for a further thirty minutes then allowed to warm to room temperature. After three hours, it was poured into water, extracted with ethyl acetate and the extracts washed successively with dilute hydrochloric acid, water, aqueous sodium bicarbonate solution, and brine. After drying over magnesium sulphate, the extracts were evaporated under reduced pressure to give the title compound (5.62 g) as an orange gum, sufficiently pure to be used in Step 4.

NMR ($CDCl_3$): δ 4.7(4 H,dd), 5.1 (1 H,s), 7.3(12 H,m), 7.8(1 H,dd), 7.85(1 H,s), 8.5 (1 H,bs).

Step 4 Preparation of 2,2-dibenzyloxy-N-benzyloxymethyl-N(3-trifluoromethylphenyl)-acetamide 2,2-Dibenzyloxy-N(3-trifluoromethylphenyl)acetamide, (4.75 g, prepared as described in Step 3), benzyl chloromethylether (1.79 g) and tetrabutylammonium iodide (100 mg) were added successively to a vigorously stirred mixture of aqueous sodium hydroxide solution (100 ml, 50%) and dichloromethane (100 ml). After stirring for eighteen hours, the mixture was extracted several times with dichloromethane and the extracts washed with brine. After drying over magnesium sulphate, the extracts were evaporated under reduced pressure. The residue was chromatographed on silica, using hexane-ethyl acetate (4:1) as eluant, to give the title compound (2.87 g). NMR ($CDCl_3$): δ 4.6(6 H,m), 4.9(1 H,bs), 5.15(2 H,bs), 7.3(18 H,m), 7.55(1 H,s).

Step 5 Preparation of 5-hydroxy-3(3-trifluoromethylphenyl)oxazolidin-4-one

A mixture of 2,2-dibenzyloxy-N-benzyloxymethyl-N(3-trifluoromethylphenyl)-acetamide (0.27 g, prepared as described in Step 4), 10% palladium on carbon (50 mg), trifluoroacetic acid (1 ml) and dichloromethane (50 ml) was stirred under an atmosphere of hydrogen for five hours. It was filtered through Hyflo Supercel™, evaporated under reduced pressure and chromatographed on silica, using dichloromethane-ethanol (49:1) as eluant to give the title compound (0.07 g) as a waxy solid, m.p. 75°–76° C. $^1$H NMR (CDCl$_3$): δ 5.35(1 H,bs), 5.45(1 H,d), 5.7(2 H,m), 7.5(2 H,m), 7.65 (1 H,d), 7.7 (1 H,s).

Step 6 5-t-Butylcarbamoyloxy-3(3-trifluoromethylphenyl)oxazolidin4-one The title compound was prepared by the method described in Step 5 of Example 2 below. Characterising data are given in Example 2.

EXAMPLE 2 Preparation of 5-(t-Butylcarbamoyloxy)-3-(3-trifluoromethylphenyl)oxazolidin-4-one Step 1 Preparation of 2-(methylthio)-N-(3-trifluoromethylphenyl)acetamide 3-Trifluoromethylaniline (16.1 g) was added dropwise to a rapidly stirred suspension of hexane-washed sodium hydride (4.0 g, 60% in mineral oil) in dimethylsulphoxide (50 ml) under a nitrogen atmosphere, with water bath cooling to 20° C. After 30 minutes ethyl (methylthio)acetate (14.7 g) was added dropwise with cooling to 20° C. After stirring for 3 hours half-saturated aqueous potassium dihydrogen phosphate (300 ml) was added cautiously with cooling to 20° C. The mixture was extracted with diethyl ether (5×100 ml), the extract washed with water (2×50 ml), dried over sodium sulphate, filtered and ether evaporated under reduced pressure to leave the crude product as a yellow solid (23.8 g). A sample was recrystallised from hexane solution for analysis. m.p. 75°–77° C. $^1$H NMR (CDCl$_3$): δ 2.21(3 H,s); 3.38(2 H,s); 7.45–7.85(4 H,m); 8.85(1 H,bs).

Step 2 Preparation of N-(Ethoxymethyl)-N-(3-trifluoromethylphenyl)-2-(methylthio)acetamide Chloromethyl ethylether (18.1 g) was added dropwise, during 20 minutes, to a vigorously stirred mixture of crude product of Step 1 (21.8 g) dissolved in dichloromethane (50 ml), 52% aqueous sodium hydroxide (34 g) and benzyl triethylammonium chloride (0.2 g), with water-bath cooling to 20° C. After 30 minutes the mixture was treated with saturated aqueous potassium dihydrogen phosphate until pH 8, at 20° C., extracted with dichloromethane (5×100 ml), the extract dried over sodium sulphate, filtered and concentrated under reduced pressure to give the crude product as a yellow oil (27.5 g). $^1$H NMR (CDCl$_3$): δ 1.23(3 H,t); 2.21(3 H,s); 3.0(2 H,s); 3.68(2 H,bq); 5.1(2H,s); 7.58(4 H,m).

Step 3 Preparation of N-(Ethoxymethyl)-N-(3-trifluoromethylphenyl)-2-(methylsulphinyl)acetamide A solution of sodium periodate (20.5 g) in water (190 ml) was added dropwise to a stirred solution of crude product of Step 2 in ethanol (850 ml) at 5° C. The mixture was allowed to reach 20° C. gradually and stirred for 24 hours, then concentrated under reduced pressure. The concentrate was extracted with dichloromethane (500 ml), the extract dried over sodium sulphate, filtered and concentrated under reduced pressure to give the crude product as a brown oil (27.5 g). $^1$H NMR (CDCl$_3$): δ 1.24(3 H,t); 2.76(3 H,s); 3.56(2 H,s); 3.67(2 H, 5.12(2 H,s); 7.51–7.69(4 H,m).

Step 4 Preparation of 5-Hydroxy-3-(3-trifluoromethylphenyl)-oxazolidin4-one

Trifluoroacetic anhydride (17.6 g) was added dropwise to a stirred solution of crude product of Step 3 in tetrahydrofuran (220 ml) with water bath cooling to 20° C. After 2 hours the mixture was left to stand for 20 hours. A solution of sodium hydrogen carbonate (14.1 g) in water (220 ml) was added during 5 minutes with stirring and cooling to 20° C. After 30 minutes the mixture was refluxed for 4½ hours, cooled to 25° C., extracted with dichloromethane (3×300 ml), the extract dried over magnesium sulphate, filtered and concentrated under reduced pressure to give a brown oil (21.4 g). The brown oil (20.09 g) was dissolved in 1,4-dioxane (500mi) and hydrogen chloride gas bubbled in for 3¼ hours, with stirring, at 23° C. The mixture was left in a stoppered flask for 20 hours, concentrated under reduced pressure, dissolved in dichloromethane (400 ml), neutralised with a minimum of saturated aqueous sodium hydrogen carbonate, dried over magnesium sulphate, filtered and concentrated under reduced pressure to a brown oil (21.9 g). The oil was subjected to column chromatography on silica gel, gradient eluting with dichloromethanet-butyl methylether mixtures to give the crude product as a yellow gum (4.7 g). The gum was crystallised from hexane solution to give a yellow solid. $^1$H NMR (CDCl$_3$): δ 4.43(1 H,bs); 5.49(1 H,s); 5.68(2 H,m); 7.49–7.8(4 H,m).

Step 5 Preparation of 5 -(t-Butylcarbamoyloxy)-3 -(3-trifluoromethylphenyl)oxazolidin-4-one Triethylamine (0.16 g) was added dropwise to a stirred solution of crude product of Step 4 (0.4 g) and t-butylisocyanate (0.32 g) in dichloromethane (5 ml). After 5 hours the mixture concentrated under reduced pressure to a brown gum. The gum was subjected to column chromatography on silica gel, eluting with hexane, t-butyl methylether mixtures to give a yellow gum which was crystallised from hexane solution to give the product as a white solid (0.11 g, m.p. 125°–6° C). $^1$H NMR (CDCl$_3$: δ 1.34(9 H,s); 4.86(1 H,bs); 5.53(1 H,d); 6.19(1 H,d); 7.5–7.8(4 H,m).

EXAMPLE 3 Preparation of 5-(3-alkyl-1-t-butyl-3-ureido)-3-(3-trifluoromethyiphenyl)oxazolidin-4-one.

Step 1 Preparation of 5-chloro-3-(3-trifluoromethylphenyl) oxazolidin-4-one

Methanesulphonyl chloride (16 mg) was added to a stirred solution of 5-hydroxy-3-(3-trifluoromethylphenyl)oxazolidin-4-one (27 mg, Example 2, Step 4) in diethyl ether (1 ml). After 5 minutes triethylamine (18 mg) was added and the mixture stirred for 20 hours. Water (1 ml) was added, the mixture extracted with ether (3×5 ml), the extract dried over magnesium sulphate, filtered and concentrated under reduced pressure to give the crude product as a yellow oil (22 mg). $^1$H NMR (CDCl$_3$): δ 5.56(1 H,d); 5.72(1 H,d); 6.3(1 H,s); 7.5–7.8(4 H,m).

Step 1 and 2 Preparation of 5-(allylamino)-3-(3-trifluoromethylphenyl)oxazolidin4-one Methanesulphonyl chloride (0.9 g) dissolved in diethylether (2 ml) was added to a stirred solution of 5-hydroxy-3-(3-trifluoromethylphenyl)oxazolidin4-one (1.0 g, Example 2, Step 4) in dichloromethane (6 ml). Triethylamine (0.8 g) dissolved in ether (2 ml) was added and the mixture allowed to exotherm to 35° C. After 2 hours the mixture was cooled in an ice-water bath and a solution of allylamine (0.92 g) in ether (2 ml) added dropwise. After 1 hour the mixture was treated with aqueous sodium chloride (20 ml), extracted with ether (3×80 ml), the extract dried over magnesium sulphate, filtered and concentrated under reduced pressure to give the crude product as a yellow gum (1.3 g). $^1$H NMR (CDCl$_3$): δ 3.49(2 H,d); 5.13(1 H,dd); 5.21 (1 H,s); 5.3(1 H,m); 5.44(1 H,d); 5.48(1H,dd); 5.9(1 H,m); 7.5–7.8(4 H,m).

Step 3 Preparation of 5-(3-allyl-1-t-butyl-3-ureido)-3-(3-trifluoromethylphenyl)oxazolidin-4-one A solution of the product of Step 2 (0.43 g) in t-butylisocyanate (2 ml) was stirred for 2 hours then left for 20 hours. The mixture was concentrated under reduced pressure to give a yellow gum which was subjected to column chromatography on silica gel, eluting with dichloromethane: t-butylmethylether 98:2. This gave a yellow solid which was recrystallised from hexane solution to give the product as a white solid (0.21 g). m.p. 149°–150° C. $^1$H NMR (CDCl$_3$): δ 1.31(9 H,s); 3.86(2 H,m); 4.73(1 H,s); 5.32(1 H,d); 5.45(1 H,d); 5.46(1 H,dd); 5.56(1 H,t); 5.88(1 H,s); 5.95(1 H,m); 7.5–7.8(4 H,m).

EXAMPLE 4 Preparation of 5-[N-(N-allyl-2-t-butylacetamido)]-3-(3-tri-fluoromethylphenyl)oxazolidin-4-one Pyridine (0.24 g) was added dropwise to a stirred solution of t-butylacetylchloride (0.4 g) in dichloromethane (2 ml) and the resulting solution added dropwise to a stirred solution of 5-(allylamino)-3-(3-trifluoromethylphenyl)oxazolidin-4-one (0.43 g, Example 3 Step 2) in dichloromethane (8 ml) at 7° C. After stirring at 7° C. for 2 hours aqueous sodium chloride (10 ml) was added, the mixture extracted with diethylether (3×50 ml), the extract dried over magnesium sulphate, filtered and concentrated under reduced pressure to give a yellow gum. The gum was subjected to column chromatography on silica gel eluting with dichloromethane: t-butyl methylether 99:1 to give a yellow solid which yielded the product as a white solid (0.26 g) on trituration with cold hexane. m.p. 92°–93° C. 1 H NMR (CDCl$_3$): δ 1.07(9 H,s); 2.26(2 H,q); 4.13(2 H,d); 5.32(1 H,d); 5.33(1 H,s); 5.47(1 H,d); 5.62(1 H,s); 5.89(1 H,m); 7.4–7.8(4 H,m).

EXAMPLE 5 Preparation of 5-[2-(2-methylbutyl)carbamoyloxy]-3-(3-tri-fluoromethylphenyl)oxazolidin-4-one This compound was prepared by a method analogous to Example 2. m.p. 88°–89° C. $^1$H NMR (CDCl$_3$): δ 0.88(3 H,t); 1.29(6 H,s); 1.68(2 H,q); 4.77(1 H,bs); 5.54(1 H,t); 6.19(1 H,d); 7.5–7.8(4 H,m).

EXAMPLE 6 Preparation of 5-[2-(2-methyl-3-butynyl)carbamoyloxy]-3-(3-tri-fluoromethyiphenyl)oxazolidin-4-one This compound was prepared by a method analogous to Example 2. $^1$H NMR (CDCl$_3$): δ 1.64(3 H,s); 1.65(3 H,s); 2.36(1 H,s); 5.14(1 H,bs); 5.54(1 H,d); 5.66(1 H,t); 6.24(1 H,d); 7.5–7.8(4 H,m).

EXAMPLE 7 Preparation of 5-[2-(2-methyl-3-butenyl)carbamoyloxy]-3-(3-tri-fluoromethylphenyl)oxazolidin-4-one This compound was prepared by partial hydrogenation of the product of Example 6 over a Lindlar catalyst. m.p. 89°–91° C. $^1$H NMR (CDCl$_3$): δ 1.44(6 H,s); 4.96(1 H,bs); 4.96(1 H,bs); 5.09(1 H,d); 5.15(1 H,d); 5.53(1 H,d); 5.65(1 H,dd); 5.97(1 H,dd); 6.19(1 H,d); 7.57–7.8(4 H,m).

EXAMPLE 8 Preparation of 5-(3-methyl-1-t-butyl-3-ureido)-3-(3-tri-fluoromethylphenyl)oxazolidin-4-one This compound was prepared by a method analogous to Example 3. m.p. 114°–116° C. $^1$H NMR (CDCl$_3$): δ 1.37(9 H,s); 2.91 (3 H,s); 4.53(1 H,bs); 5.47(1 H,t); 5.56(1 H,t); 6.08(1 H,s); 7.5–7.9(4 H,m).

The precursor compound was 5-(methylamino)-3-(3-trifluoromethylphenyl)oxazolidin-4-one. $^1$H NMR (CDCl$_3$): δ 2.57(3 H,m); 5.2(1 H,d); 5.46(1 H,d); 5.5(1 H,dd); 7.5–7.9(4 H,m).

EXAMPLE 9 Preparation of 5-[N-(2-t-butyl-N-methylacetamido)]-3-(3-tri-fluoromethylphenyl)oxazolidin-4-one This compound was prepared by a method analogous to Example 4. m.p. 116°–117° C. $^1$H NMR (CDCl$_3$): Major rotamer: δ 1.09(9 H,s); 2.32(2 H,s); 3.13(3 H,s); 5.5( 5.6(1 H,t); 5.9(1 H,bs); 7.5–7.8(4 H,m). The precursor compound is detailed in Example 8.

EXAMPLE 10 Preparation of 5-[N-(2-t-butylacetamido)]-3-(3-trifluoro-methylphenyl)oxazolidin-4-one This compound was prepared by a method analogous to Example 4. m.p. 159°–161° C. $^1$H NMR (CDCl$_3$): δ 1.07(9 H,s); 2.14(2 H,s); 5.49(1 H,d); 5.53(1 H,dd); 5.59(1 H,t); 6.41 (1 H,bd); 7.5–7.8 (4 H,m).

The precursor compound was 5-amino-(3-trifluoromethylphenyl)oxazolidin4-one. $^1$H NMR (CDCl$_3$): δ 2.35(2 H,bd); 5.23(1 H,t); 5.42(1 H,d); 5.49(1 H,dd); 7.5–7.8(4 H,m).

EXAMPLE 11

5-(t-butylcarbamoyloxy)-3-(3-trifluoromethoxyphenyl)-oxazolidin-4-one

This compound was prepared using a similar method to that described in Example 2.
Step 1 Preparation of 2-(methylthio)-N-(3-trifluoromethoxyphenyl)acetamide This compound was prepared using a method similar to that described in Example 2, Step 1.
$^1$H NMR(CDCl$_3$): δ 2.20(3 H,s); 3.35(2 H,s); 7.0(1 H,d); 7.35(1 H,t); 7.45(1 H,d); 8.80(1 H,bs).
MPt: 43.5°–45° C.
Step 2 Preparation of N-(ethoxymethyl)-N-(3-trifluoromethoxyphenyl)-2-(methylthio) acetamide This compound was prepared using a similar method to that describe in Example 2, Step 2.
$^1$H NMR(CDCl$_3$): δ 1.22(3 H,t); 2.22(3 H,bs); 3.02(2 H,bs); 3.68(2 H,m); 5.10(2 H,s) 7.29(3 H,m); 7.47(1 H,t).
Step 3 Preparation of N-(ethoxymethyl)-N-(3-trifluoromethoxyphenyl)-2-(methylsulphinyl) acetamide This compound was prepared using a method similar to that described in Example 2, Step 3.
$^1$H NMR(CDCl$_3$): δ 1.24(3 H,t); 2.76(3 H,s); 3.59(2 H,d); 3.67(2 H,q); 5.11(2 H,d); 7.12(1 H,s); 7.22–7.36(2 H,m); 7.51 (1 H,t).
Step 4 Preparation of 5-hydroxy-3-(3-trifluoromethoxyphenyl)oxazolidin-4-one This compound was prepared using a method similar to that described in Example 2, Step 4.
$^1$H NMR(CDCl$_3$): δ 5.44(1 H,s); 5.65(2 H,s); 7.06–7.16(1 H,m);7.37–7.45(2 H,m); 7.61(1 H,s).
Step 5 Preparation of 5-(t-butylcarbamoyloxy)-3-(3-trifluoromethoxyphenyl)-oxazolidin-4-one The title compound was prepared using a method similar to that described in Example 2, step 5.
$^1$H NMR(CDCl$_3$): δ 1.36(9 H,s); 4.86(1 H,bs); 5.50(1 H,d); 5.63(1 H,m); 6.21(1 H,s); 7.62(1 H,s). 7.16(1 H,m); 7.45(2 H,m); 7.62(1 H,s).
MPt: 85.5°–87° C.

EXAMPLE 12

5-[2-(2-methyl-3-butynyl)carbamoyloxy]-3-(3-trifluoromethoxyphenyl)oxazolidin-4-one This compound was prepared using a similar method to that described in Example 2

¹H NMR(CDCl₃): δ 1.65(6 H,s); 2.37(1 H,s); 5.13(1 H,bs); 5.50(1 H,d); 5.63(1 H,m); 6.24(1 H,s); 7.08–7.14(1 H,m); 7.39–7.49(2 H,m); 7.61 (1 H,s).
MPt: 95°–97° C.

EXAMPLE 13

5-[2-(2-methyl-3-butenyl)carbamoyloxy]-3-(3-trifluoromethoxyphenyl) oxazolidin-4-one This compound was prepared using a similar method to that described in Example 7.
¹H NMR(CDCl₃): δ 1.42(6 H,s); 4.98(IH,bs); 5.08(1 H,d); 5.16(1 H,d); 5.50(1 H,d); 5.61(1 H,m); 6.19(1 H,s); 7.11(1 H,m); 7.37–7.47(2 H,m); 7.60(1 H,s).
MPt: 80.5°–82° C.

EXAMPLE 14

5-[2-(2-methylbutyl)carbamoyloxy]-3-(3-trifluoromethoxyphenyl)oxazolidin-4-one

This compound was prepared using a similar method to that described in Example 2.
¹H NMR(CDCl₃): δ 0.88(3 H,t): 1.30(6 H,s); 1.68(2 H,q); 4.78(1 H,bs); 5.50(1 H,d) 5.62(1 H,m); 6.20(1 H,s); 7.08–7.16(1 H,m); 7.40–7.50(2 H,m); 7.62(1 H,s).
MPt: 74°–77° C.

EXAMPLE 15

5-[N-(2-t-butyl-N-methylacetamido)]-3-(3-trifluoromethoxyphenyl)oxazolidin-4-one This compound was prepared using a similar method to that described in Example 4 from the intermediate 5-[methylamino]-3-(3-trifluoromethoxyphenyl)oxazolidin-4-one. This intermediate was prepared using a method similar to that described in Example 3, Step 2.
Intermediate:
¹H NMR(CDCl₃): δ 2.57 (3 H,s); 5.18(1 H,s); 5.41(1 H,m); 5.47(1 H,m); 7.05–7.13(1 H,m); 7.13–7.33(2 H,m); 7.61(1 H,s).
Product
¹H NMR(CDCl₃): δ (9 H,s); 2.32(2 H,s); 3.12(3 H,s); 5.47(1 H,s); 5.58(1 H,s) 7.03–7.17(1 H,m); 7.41–7.48(2 H,m); 7.61 (1 H,s).
MPt: 99.5°–102° C.

EXAMPLE 16

5[N-(2-t-butyl-N-ethylacetamido)]-3-(3-trifluoromethoxyphenyl)oxazolidin-4-one

This compound was prepared using a similar method to that described in Example 4 from the intermediate 5-(N-ethylamino)-3-(3-trifluoromethoxyphenyl)oxazolidin-4-one which was prepared using a method similar to that described in Example 3, Step 2.
Intermediate:
¹H NMR(CDCl₃): δ 1.25(3 H,t); 2.90(2 H,q); 4.27(1 H,bs); 5.20(1 H,s); 5.40(1 H,m 5.46(1 H,m); 7.04–7.11(1 H,m); 7.38–7.50(2 H,m); 7.60(1 H,s).
Product:
¹H NMR(CDCl₃): δ 1.08(9 H,s); 1.32(3 H,t); 2.29(2 H,d); 3.43–3.64(2 H,m); 5.30(1 H,bs); 5.45(1 H,s); 5.58(1 H,bs); 7.0–7.19(1 H,m); 7.39–7.45(2 H,m); 7.60(1 H,bs).
MPt: 95°–97° C.

EXAMPLE 17

5-[N-(2-t-butylacetamido)]-3-(3-trifluoromethoxyphenyl) oxazolidin-4-one

This compound was prepared using a similar method to that described in Example 4 from the intermediate 5-amino-3-(3-trifluoromethoxyphenyl)oxazolidin-4-one which was prepared using a method similar to that described in Example 3, Step 2.
Intermediate:
¹H NMR(CDCl₃): δ 1.62(2 H,bs); 5.20(1 H,bs); 5.37(1 H,d); 5.45(1 H,d); 7.03–7.13(1 H,m); 7.32–7.47(2 H,m); 7.60(1 H,s).
Product:
¹H NMR(CDCl₃): δ 1.07(9 H,s); 2.14(2 H,s); 5.45(1 H,s); 5.55(2 H,m); 6.39(1 H,bd); 7.05–7.13(1 H,m); 7.38–7.44(2 H,m); 7.60(1 H,s).
MPt: 145°–148° C. (dec).

EXAMPLE 18

5-Hydroxy- 3(3-trifluoromethoxyphenyl)oxazolidin-4-one
Step 1 Preparation of 2,2-dibenzyloxy-N(3-trifluoromethoxyphenyl)acetamide A solution of dibenzyloxyacetic acid (23.1 g) in diethyl ether (200 ml) was added to a solution of 3-trifluoromethoxyaniline (15 g) in diethyl ether (100 ml). A solution of dicyclohexyldicarbodiimide (16.5 g) in diethyl ether (100 ml) was then added in two portions. The mixture was left overnight and the precipitated solid then filtered off and the filtrate diluted with a mixture of diethyl ether and hexane (5:95) and refrigerated for an hour. The solid which separated was collected and washed with hexane, giving the title compound (10 g) with a melting point of 75°–77° C.
Step 2 Preparation of 2,2-dibenzyloxy-N-benzyloxymethyl-N(3-trifluoromethoxyphenyl)acetamide A solution of the amide prepared as described in Step 1 (16.87 g) in dichloromethane (100 ml) was treated with a solution of sodium hydroxide (7.605 g) in water (30 ml) followed by benzyltriethylammonium chloride (0.4 g). Benzyl chloromethyl ether (8.16 ml) was added over a period of 15 minutes while the mixture was cooled to keep it below 15° C. Gas chromatography showed that the mixture contained about 20% of the starting material. The organic layer was separated, dried and evaporated and taken up again in tetrahydrofuran (100 ml) and sodium hydride (0.3 g) added. The mixture was stirred for two hours and benzyl chloromethyl ether (1.565 g) added over a period of five minutes. Stirring was continued for an hour. The mixture was then warmed to 30° C. for 30 minutes, when all the sodium hydride had dissolved. More benzyl chloromethyl ether (1.565 g) was added and the mixture stirred for another five hours. The reaction mixture was then diluted with water and extracted with ethyl acetate. Evaporation of the extracts yielded a yellow oil (24.2 g) which was used directly in the next step below.
Step 3
Preparation of 5-hydroxy-3(3-trifluoromethoxyphenyl) oxazolidin4-one A solution in ethanol (30 ml) of the tribenzyl compound prepared in Step 2 (1.3 g) was stirred with 5% palladium on charcoal catalyst (0.1 g) and trifluoroacetic acid under an atmosphere of hydrogen for 7 hours. The reaction mixture was filtered and evaporated to give a yellow oil. This was dissolved in a mixture of ethyl acetate and hexane (1:9) and chromatographed on a silica column to give a yellow oil (0.41 g). The mass spectrum showed that the oil contained the title compound together with a proportion of N-benzyloxymethyl-N-(3-trifluoromethoxyphenyl)acetic acid Thus, the process of the present invention makes it possible to synthesise oxazolidinone compounds of general formula II in high yield and this in turn increases the possibilities for a large scale synthesis of herbicides of general formula I.

We claim:

1. A process for the synthesis of a compound of general formula II:

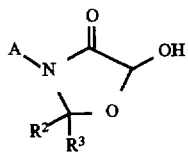

wherein:

$R^2$ and $R^3$ are each independently hydrogen or $C_1$–$C_4$ alkyl; A is an aromatic or heteroaromatic ring system optionally substituted with one or more substituents selected from: halogen, $C_1$–$C_{10}$ hydrocarbyl, —S($C_1$–$C_{10}$ hydrocarbyl), —SO($C_1$–$C_{10}$ hydrocarbyl), —SO$_2$($C_1$–$C_{10}$ hydrocarbyl), cyano, nitro, SCN, SiR$^c_3$ where each R$^c$ is independently $C_1$–$C_4$ alkyl or phenyl, COR$^7$, CR$^7$NOR$^8$, NHOH, ONR$^7$R$^8$, SF$_5$, COOR$^7$, SO$_2$NR$^7$R$^8$, OR$^9$ or NR$^{10}$R$^{11}$; and in which any ring nitrogen atom may be quaternised or oxidised;

alternatively, any two substituents of the group A may combine to form a fused 5- or 6-membered saturated or partially saturated carbocyclic or heterocyclic ring in which any carbon or quaternised nitrogen atom may be substituted with any of the groups mentioned above for A or in which a ring carbon atom may be oxidised;

$R^7$ and $R^8$ are each independently hydrogen or $C_1$–$C_{10}$ hydrocarbyl;

$R^9$ is hydrogen, $C_1$–$C_{10}$ hydrocarbyl, SO$_2$($C_1$–$C_{10}$ hydrocarbyl), CHO, CO($C_1$–$C_{10}$ hydrocarbyl), COO ($C_1$–$C_{10}$ hydrocarbyl) or CONR$^7$R$^8$;

$R^{10}$ and $R^{11}$ are each independently hydrogen, $C_1$–$C_{10}$ hydrocarbyl, O($C_1$–$C_{10}$ hydrocarbyl), SO$_2$($C_1$–$C_{10}$ hydrocarbyl), CHO, CO($C_1$–$C_{10}$ hydrocarbyl), COO ($C_1$–$C_{10}$ hydrocarbyl) or CONR$^7$R$^8$;

any of the hydrocarbyl groups within the group A may optionally be substituted with halogen, hydroxy, SO$_2$NR$^a$R$^b$ where R$^a$ and R$^b$ are independently hydrogen or $C_1$–$C_6$ alkyl, cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide in which the groups attached to the N atom may be hydrogen or lower hydrocarbyl optionally substituted with halogen; alkoxy carbonyl wherein the alkoxy group may have from 1 to 6 or more carbon atoms, or aryl;

the process comprising cyclising a compound of general formula VII:

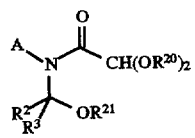

wherein A, $R^2$ and $R^3$ are as defined for general formula II, $R^{20}$ is hydrogen, benzyl or benzyl substituted with up to five substituents selected from halo, $C_1$–$C_6$ alkyl, O($C_1$–$C_6$ alkyl) or nitro and $R^{21}$ is $C_1$–$C_8$ alkyl, benzyl or benzyl substituted with up to five of the substituents mentioned above for $R^{20}$.

2. A process as claimed in claim 1, wherein $R^{20}$ is benzyl or substituted benzyl and in which the cyclisation is achieved by hydrogenation over a palladium catalyst in the presence of an acid.

3. A process as claimed in claim 2, wherein $R^{21}$ is benzyl or substituted benzyl.

4. A process as claimed in claim 1, wherein $R^{20}$ is hydrogen and in which the cyclisation is carried out by reaction with an acid.

5. A process as claimed in claim 4, wherein the cyclisation is carried out using gaseous hydrogen chloride in an organic solvent.

6. A process as claimed in claim 4, wherein $R^{21}$ is $C_1$–$C_8$ alkyl.

7. A process as claimed in claim 1, wherein the compound of general formula VII is prepared from a compound of general formula VIII:

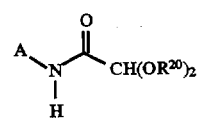

wherein A and $R^{20}$ are as defined for formula VII, by reaction with a compound of formula IX:

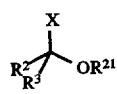

where X is a leaving group and $R^2$, $R^3$ and $R^{21}$ are as defined for formula VII; in a mixed aqueous organic solvent and in the presence of a base and a phase transfer catalyst.

8. A process as claimed in claim 1, wherein the compound of general formula VII is prepared from a compound of general formula XII:

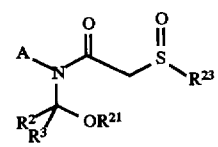

wherein A, $R^2$, $R^3$ and $R^{21}$ are as defined for general formula VII and $R^{23}$ is $C_1$–$C_6$ alkyl, benzyl, or aryl, any of which may optionally be substituted by the substituents mentioned in claim 1 for $R^{20}$; by a two stage process in which the compound is either treated with a strong acid or with an acylating agent and then heated with a weak base.

9. A process for the preparation of a compound of general formula I:

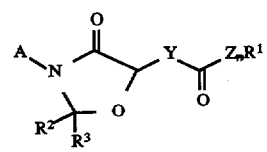

wherein A, $R^2$ and $R^3$ are as defined for general formula II;

Z is O, S or NR$^4$;

$R^4$ is hydrogen or $C_1$–$C_4$ alkyl;

n is 0 or 1;

Y is O, S or NR$^6$;

$R^6$ is hydrogen, CHO, or $C_1$–$C_{10}$ hydrocarbyl, which may be substituted with up to two substituents chosen from OR$^{16}$, COR$^{16}$, COOR$^{16}$, OCOR$^{16}$, CN, halogen, S(O)$_p$R$^{16}$, NR$^{16}$R$^{17}$, NO$_2$, NR$^{16}$COR$^{17}$, NR$^{16}$CONR$^{17}$R$^{18}$, CONR$^{16}$R$^{17}$ or heterocyclyl;

$R^{16}$, $R^{17}$ and $R^{18}$ are each, independently, hydrogen, $C_1$–$C_6$ hydrocarbyl or $C_1$–$C_6$ halohydrocarbyl;

p is 0, 1 or 2;

alternatively:

when Y is $NR^6$ and either Z is $NR^4$ or n is 0, $R^6$ and the substituents of Z or $R^1$ may together form a bridge represented by the formula —$Q^1$—$Q^2$— or —$Q^1$—$Q^2$—$Q^3$—, where $Q^1$, $Q^2$ and $Q^3$ each independently represent $CR^{12}R^{13}$, =$CR^{12}$, CO, $NR^{14}$, =N, O or S; each of $R^{12}$ and $R^{13}$ independently represents hydrogen, $C_1$–$C_4$ alkyl, OH or halogen;

$R^{14}$ represents hydrogen or $C_1$–$C_4$ alkyl;

$R^1$ is hydrogen or $C_1$–$C_{10}$ hydrocarbyl or heterocyclyl having 3 to 8 ring atoms, either of which may optionally be substituted with halogen, hydroxy, $SO_2NR^aR^b$ where $R^a$ and $R^b$ are independently hydrogen or $C_1$–$C_6$ alkyl, $SiR^c_3$ where each $R^c$ is independently $C_1$–$C_4$ alkyl or phenyl, cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide in which the groups attached to the N atom may be hydrogen or optionally substituted lower hydrocarbyl; alkoxy carbonyl wherein the alkoxy group may have from 1 to 6 or more carbon atoms, or aryl.

10. A process as claimed in claim 9, wherein the compound of general formula II is converted to a compound of general formula I in which Y is O by reaction with a compound of general formula XVI, XVII, XVIII, XIX or XX:

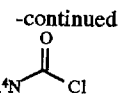   XVI

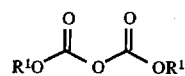   XVII $R^1$—N=C=O   XVIII

-continued

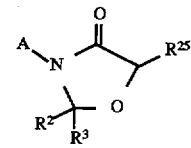   XIX

XX wherein $R^1$ and $R^4$ are as defined for formula I.

11. A process as claimed in claim 9, wherein the compound of general formula II is converted to a compound of general formula XXI:

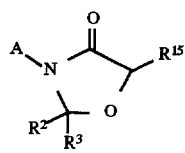   XXI wherein A, $R^2$ and $R^3$ are as defined for general formula II and $R^{25}$ is chloro, methane sulfonyloxy or toluene sulfonyloxy, by reaction with methane sulfonyl chloride or toluene sulfonyl chloride as appropriate; the compound of general formula XXI is converted into a compound of general formula XXII:

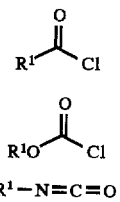   XXII wherein A, $R^2$ and $R^3$ are as defined for general formula I and $R^{15}$ is $NHR^6$ where $R^6$ is as defined for general formula I; by reaction with ammonia or an amine of formula $NH_2R^6$; and the compound of general formula XXII is reacted with a compound of general formula XVI, XVII, XVIII, XIX or XX as defined in claim 10 to give a compound of general formula I in which Y is $NR^6$.

* * * * *